(12) United States Patent
Thirup et al.

(10) Patent No.: US 11,564,404 B2
(45) Date of Patent: Jan. 31, 2023

(54) VERTICAL PLUG-FLOW PROCESS FOR BIO-CONVERSION EMPLOYING MICROORGANISMS

(71) Applicant: Hamlet Protein A/S, Horsens (DK)

(72) Inventors: Laila Thirup, Skanderborg (DK); Jonatan Ahrens Dickow, Stouby (DK); Katrine Hvid Ellegård, Ry (DK); Stig Victor Petersen, Beder (DK); Svend Andreas Geleff, Rødding (DK)

(73) Assignee: Hamlet Protein A/S, Horsens (DK)

( * ) Notice: Subject to any disclaimer, the term of this patent is extended or adjusted under 35 U.S.C. 154(b) by 83 days.

(21) Appl. No.: 16/955,328

(22) PCT Filed: Dec. 20, 2018

(86) PCT No.: PCT/EP2018/086282
§ 371 (c)(1),
(2) Date: Jun. 18, 2020

(87) PCT Pub. No.: WO2019/122181
PCT Pub. Date: Jun. 27, 2019

(65) Prior Publication Data
US 2021/0000137 A1    Jan. 7, 2021

(30) Foreign Application Priority Data

Dec. 22, 2017    (EP) .................... 17210105

(51) Int. Cl.
*A23K 10/12*    (2016.01)
*A23K 10/14*    (2016.01)
*A23L 33/135*    (2016.01)
*A23J 1/14*    (2006.01)

(52) U.S. Cl.
CPC .............. *A23K 10/12* (2016.05); *A23J 1/14* (2013.01); *A23K 10/14* (2016.05); *A23L 33/135* (2016.08); *A23Y 2220/00* (2013.01); *A23Y 2240/00* (2013.01); *A23Y 2280/00* (2013.01); *A23Y 2300/00* (2013.01)

(58) Field of Classification Search
CPC ....... A23K 10/12; A23K 10/14; A23L 33/135; A23J 1/14; A23Y 2220/00; A23Y 2240/00; A23Y 2280/00; A23Y 2300/00
USPC ......................................................... 426/53
See application file for complete search history.

(56) References Cited

U.S. PATENT DOCUMENTS 7,452,425 B1    11/2008  Langhauser
2009/0142848 A1    6/2009  Wyman et al.

FOREIGN PATENT DOCUMENTS

| EP | 1 145 648 A1 | 10/2001 |
|---|---|---|
| EP | 1 264 784 A1 | 12/2002 |
| EP | 2 453 004 B1 | 11/2014 |
| EP | 3 101 136 A1 | 12/2016 |
| WO | WO-01/54519 A1 | 8/2001 |
| WO | WO-2011/137237 | 11/2011 |
| WO | WO-201 3/050456 A1 | 4/2013 |

OTHER PUBLICATIONS

Waters, A.J. et al. PowderTechnol. 113: 168-175 (Year: 2000).*
Encyclopedia of Food Microbiol. vol. 1-3. p. 664 (Year: 2000).*
Khanahmadi et al., "Continuous solid-state fermentation as affected by substrate flow pattern," Chemical Engineering Science, vol. 61, No. 8, pp. 2675-5687 (Jan. 2006).
Li et al., "Solid-state anaerobic digestion for methane production from organic waste," Renewable and Sustainable Energy Reviews, vol. 15, No. 1, pp. 821-826 (2011).
O'Connell et al., "Metabolism of four α-Glycosidic Linkage-Containing Oligosaccharides by *Bifidobacterium breve* UCC2003," Applied and Environmental Microbiology, vol. 79, No. 20, pp. 6280-6292 (Aug. 2013).
Foreign Search Report with English Translation issued in RU Patent Application No. 2020123071/10 dated Jul. 12, 2022.
Tisseyre B et al. Conception and characterization of a continuous plug flow bioreactor, Bioprocess Engineering, 1995, vol. 13, pp. 113-118.

\* cited by examiner

*Primary Examiner* — Hamid R Badr
(74) *Attorney, Agent, or Firm* — Foley & Lardner LLP

(57) ABSTRACT

The invention relates to a method for producing a solid transformation product of a substrate comprising the following steps: •preparing a substrate of biomass comprising carbohydrates and proteinaceous matter that originates from soya bean, rape seed, or mixtures thereof, optionally in further mixture with carbohydrates and proteinaceous matter originating from fava beans, peas, sunflower seeds, lupine, cereals, and/or grasses, •mixing said substrate with a live microorganism or a combination of live microorganisms, which live microorganism or mixture of live microorganisms is not live yeast, and adding water in an amount which provides an initial incubation mixture having a water content from 30 to 70% by weight, and a ratio of wet bulk density to dry bulk density from 0.60 to 1.45 in the resulting mixture; •incubating said initial incubation mixture for 1-240 hours at a temperature of 15-70° C.; and thereafter recovering wet solid transformation product from the incubation mixture; further comprising that the incubating step is performed as a continuous plug-flow process in a vertical, non-agitated incubation tank with inlet means for said mixture and additives and outlet means for said solid transformation product.

27 Claims, No Drawings

VERTICAL PLUG-FLOW PROCESS FOR BIO-CONVERSION EMPLOYING MICROORGANISMS

CROSS-REFERENCE TO RELATED APPLICATIONS

The present application is the U.S. National Stage of International Application No. PCT/EP2018/086282, filed Dec. 20, 2018, and claims priority to European Patent Application No. 17210105.7 filed Dec. 22, 2017.

FIELD OF THE INVENTION

The present invention relates to a solid substrate, bio-conversion method for the production of a valuable solid transformation product of the substrate wherein the bio-conversion is carried out by the use of one or more suitable microorganism by a continuous plug flow process in a vertical, non-agitated tank where the transport is mediated by gravitational force.

BACKGROUND OF THE INVENTION

There is a need for bio-products that primarily can be used as food or feed or as ingredients in food or feed. The basic constituents in such products are proteins, fats, and carbohydrates. Suitable biomasses for such products are oil bearing crops such as oilseeds, cereals, and legumes. Cereals have a protein content up to 15% e.g. in wheat, and legumes have a protein content of up to 40% e.g. in soya beans, based on dry matter.

There is a similar need for the development of bio-products comprising organic compounds, such as organic acids, e.g. formic acid, acetic acid, propionic acid, butyric acid, lactic acid, and succinic acid, or alcohols, such as ethanol, which bio-products and organic compounds can be produced in a cost-effective way in well-known processes using microorganism genera which produce one or more organic compounds as metabolic product of carbohydrate bio-conversion.

The lactic acid bacteria genera produce organic acid, in particular lactic acid and acetic acid, as their major metabolic end product of carbohydrate bio-conversion. The lactic acid bacteria genera are in particular, but are not limited to, *Lactobacillus, Leuconostoc, Pediococcus, Lactococcus, Enterococcus, Streptococcus*, and *Weisella*.

Other microorganism genera also produce acids as their metabolic end products of carbohydrate bio-conversion. Such genera which produce organic acid are in particular, but are not limited to, acid-producing *Bacillus, Bifidobacterium, Brevibacillus, Propionibacterium, Candida, Clostridium*, and *Geobacillus*.

A general problem especially related to pulses and fruits and seeds from legumes as sources of bio-product and organic acids are the content of indigestible oligosaccharides, such as stachyose and raffinose, causing flatulence and diarrhoea when fermented in the colon.

Low cost incubation methods known in the art are solid substrate or solid-state fermentation (SSF) processes performed with low water content. The process consists of a solid, moist substrate inoculated with suitable microorganisms and left for bio-conversion under temperature controlled conditions for a period of time.

Normally the substrate is incubated batch wise on flatbeds without stirring; one example of this process is known as the Koji process. Batch processes are also performed using stirring means.

Continuous SSF processes are also described in literature using the following bioreactors: Stirred tank, rotating drum and tubular flow reactors. One example of a tubular flow reactor is the screw conveyor type.

U.S. Pat. No. 4,735,724 discloses a non-mixed vertical tower anaerobic digester and a process for digestion of the biodegradable part of feedstock by methane producing microorganisms. The method is characterized in that there is a withdrawal of liquid from a middle or lower zone to the top of the tower.

EP 2 453 004 B1 discloses a method for anaerobic fermentation of organic material in a closed tank and top down feed in the tank under the action of the gravity. The method is characterized in that the fermenting mass is agitated by alternately increasing the pressure of the product gas and abruptly relieving the pressure of the product gas.

The object of the present invention is to provide an improved method for the production of a solid transformation product of a biomass substrate in a vertical, plug flow, bio-conversion process carried out by the use of one or more suitable microorganism.

Another object is to provide a method, which can be performed in a larger but simpler reactor design than the prior art design.

Yet an object is to provide an efficient and fast method for bio-conversion of biomasses, in particular soya bean or rape seed or mixtures thereof, so as to produce bio-products comprising organic compounds, such as organic acids, e.g. formic acid, acetic acid, propionic acid, butyric acid, lactic acid, and succinic acid, and alcohols, from cheap carbohydrate sources.

These objects are fulfilled with the method of the present invention.

SUMMARY OF THE INVENTION

Accordingly, in one aspect of the present invention it relates to a method for producing a solid transformation product of a substrate comprising the following steps:
- preparing a substrate of biomass comprising carbohydrates and proteinaceous matter that originates from soya bean, rape seed, or mixtures thereof, optionally in further mixture with carbohydrates and proteinaceous matter originating from fava beans, peas, sunflower seeds, lupine, cereals, and/or grasses,
- mixing said substrate with a live microorganism or a combination of live microorganisms, which live microorganism or combination of live microorganisms is not live yeast, and adding water in an amount which provides an initial incubation mixture having a water content from 30% to 70%, and a ratio of wet bulk density to dry bulk density from 0.60 to 1.45 in the resulting mixture;
- incubating said initial incubation mixture for 1-240 hours at a temperature of 15-70° C.; and recovering wet solid transformation product from the incubated mixture;
- further comprising that the incubating step is performed as a continuous plug-flow process in a vertical, non-agitated incubation tank with inlet means for said mixture and additives and outlet means for said solid transformation product.

The present method for treatment of biomass uses gravitational force to transport/move the biomass during incubation/bio-conversion. Although the use of gravity for transportation in general is straightforward, it requires careful selection of reaction conditions for the specific purpose, such as in the case of the present plug-flow process.

Normally, when the water content is increased, an incubation mixture tends to compact, by the reduction of void volume, so that the transportation behaviour is affected negatively. When a certain water content is reached the mixture is compacted to an extent so that the transportation by gravitational force is stopped. The material may stick to the walls of the reactor, or it may create sedimentation, and the uniform plug-flow is disrupted resulting in uneven retention time of the biomass.

Furthermore, if the bio-conversion is performed at elevated pressure, which may be the case under the gravity effect, the incubation reaction tends to slow down.

The solution according to the present invention to the problem connected with transportation by gravitational force of the incubation mixture is to make use of a tank as defined in the claims for incubation wherein the flow of material can be kept so high and uniform that plug-flow conditions are achieved and maintained. The flow rate is regulated by the inlet and outlet means and by the dimensions (width to height ratio) of the tank.

Furthermore, the solution according to the invention must secure balancing of the water content in the incubation mixture so that the water activity on the particle surface is sufficient for the reaction process. This is achieved by keeping the ratio wet bulk density to dry bulk density of the substrate low and within certain limits as defined in claim 1.

More specifically, the present inventors have found that the necessary uniform process can be achieved by using an initial incubation mixture having a water content from 30% to 70% by weight, and a ratio of wet bulk density to dry bulk density from 0.60 to 1.45. In combination with the present, vertical design for the plug-flow process it is possible to secure a uniform plug-flow and ensure the same processing time for the incubation mixture. Furthermore, the method of the present invention is conducted without agitation. If the water content exceeds approximately 70% by weight, the biomass cannot hold the water, and the incubation mixture becomes a slurry having a water phase and a solid phase. These two phases will not flow with the same flow rates, uniform plug flow will not be obtained, and the incubation mixture may stick to the incubator walls. A water content of more than approximately 70% will result in a ratio of wet bulk density to dry bulk density, exceeding 1.45 that is the upper limit according to the invention.

The vertical design is less expensive in investment than a horizontal design due to its larger capacity in a single production line. It is also less expensive to maintain due to less mechanical movements. The use of a non-agitated tank further contributes to reduced operational costs.

Thus, the present method allows an efficient and fast set-up of the process whereby the microorganism can propagate in liquid phase and perform bioconversion on cheap carbohydrate-based sources.

The present method is, in particular, efficient if the substrate of biomass has been pre-treated before it is mixed with the live microorganism or combination of live microorganisms, because the pre-treatment improves the access of the microorganisms to the components in the biomass which are to be transformed. The pre-treatment is typically carried out by chemical or physical pre-treatment, e.g. by means of disintegration, milling, flaking, heat treatment, pressure treatment, ultrasonic treatment, hydrothermal treatment, or acid or alkaline treatment.

The method of the invention can be used to provide a solid transformation product of the substrate which is a product of the transformation of carbohydrates and/or proteins originating from said biomass. Such solid transformation products can be used e.g. in a processed food product or as an ingredient in a food or feed product or as an ingredient of a cosmetic or a pharmaceutical product, or a nutritional supplement.

Definitions

In the context of the current invention, the following terms are meant to comprise the following, unless defined elsewhere in the description.

The terms "about", "around", "approximately", or "~" are meant to indicate e.g. the measuring uncertainty commonly experienced in the art, which can be in the order of magnitude of e.g. +/−1, 2, 5, 10, 20, or even 50%.

The term "comprising" is to be interpreted as specifying the presence of the stated part(s), step(s), feature(s), composition(s), chemical(s), or component(s), but does not exclude the presence of one or more additional parts, steps, features, compositions, chemicals or components. E.g., a composition comprising a chemical compound may thus comprise additional chemical compounds, etc.

Plug-Flow Process:

In this type of continuous process, the reaction mixture flows through e.g. a tubular or polyhedral reactor with limited back mixing. The flow is a laminar flow where the composition of the reaction mixture changes along the axial direction of the reactor, or a uniform mass flow.

Biomass:

Comprises biological material, as produced by the photosynthesis and that can be used as raw material in industrial production. In this context, biomass refers to plant matter in the form of seeds, cereals, pulses, grasses, e.g. beans and peas, etc., and mixtures thereof, and in particular fruits and seeds of legumes. Furthermore, a biomass comprising pulses is specifically applicable due to the protein content and composition.

The substrate of biomass may be disintegrated by pre-treatment, such as chemical or physical pre-treatment, e.g. by means of disintegration, milling, flaking, heat treatment, pressure treatment, ultrasonic treatment, hydrothermal treatment, or acid or alkaline treatment.

Bio-Conversion/Incubation:

Is the process to incubate cultures of microorganisms on a substrate for a specific purpose, e.g. incubating a microorganism on a carbohydrate to produce organic acids or alcohols.

Solid Transformation Product of the Substrate:

In general treatment of biomass by incubation with microorganisms can be divided into four types:

Production of biomass—cellular material

Production of extracellular components—chemical compounds, metabolites, such as acids, enzymes Production of intracellular components—enzymes, etc.

Transformation product of the substrate—the transformed substrate is the product In the present context, solid transformation product of the substrate refers to a product resulting from incubation of the selected biomass with live microorganism and optionally processing aids.

Bulk Density:

Bulk density is a parameter important for the physical behaviour of a biomass which has the form of powder, granules, and the like. The parameter is defined as weight per volume, and may be measured in, e.g., g/ml. It is not an intrinsic property, but can change depending on handling, and can be used as an index of structural changes. The density of a material is determined by placing a fixed volume of the material in a measuring cup and determining the weight or by determining the weight of a measured volume of a powder. By this test the following features can be determined:

Bulk density (also known as pour density)=mass/untapped dry volume in g/mL or kg/m$^3$;

Wet bulk density (also known as total density)=the ratio of the total mass ($M_s+M_l$) to its total volume;

$M_s$=mass of solids and $M_l$=mass of liquids.

Thus, in the context of the present invention, "dry bulk density" is the measured bulk density of the biomass without addition of water, viz. the bulk density/pour density. "Wet bulk density" is the bulk density measured after addition of a certain amount of water.

Normally, the bulk density is determined in accordance with International Standards ISO 697 and ISO 60, but due to the nature of the substances this was not applicable in the present context. The individual method used is described in the examples.

Oligosaccharides and Polysaccharides:

An oligosaccharide is a saccharide polymer containing at least two component monomer sugars. Polysaccharides are saccharide polymers containing many component monomer sugars, also known as complex carbohydrates. Examples include storage polysaccharides such as starch and structural polysaccharides such as cellulose.

Carbohydrates:

Comprise mono-, di-, oligo- and polysaccharides.

Proteinaceous Materials:

Comprise organic compounds with a substantial content of proteins made of amino acids arranged in one or more chains. At a chain length of up to approximately 50 amino acids the compound is called a peptide; at higher molecular weight the organic compound is called a polypeptide or a protein.

Fats:

Comprise esters between fatty acids and glycerol. One molecule of glycerol can be esterified to one, two and three fatty acid molecules resulting in a monoglyceride, a diglyceride or a triglyceride respectively. Usually fats consist of mainly triglycerides and minor amounts of lecithins, sterols, etc. If the fat is liquid at room temperature it is normally called oil. With respect to oils, fats, and related products in this context, reference is made to "Physical and Chemical Characteristics of Oils, Fats and Waxes", AOCS, 1996, as well as "Lipid Glossary 2", F. D. Gunstone, The Oily Press, 2004.

Glycerides:

Comprise mono-, di-, and triglycerides.

Microorganisms

Microorganisms are organisms which are microscopic, making them too small to be seen by the unaided human eye. Microorganisms include bacteria, fungi, archaea, protists and viruses. Most micro-organisms are single-celled, or unicellular organisms, but there are unicellular protists that are visible to the human eye, and some multicellular species are microscopic. Microorganisms live almost everywhere on earth where there is liquid water, including hot springs on the ocean floor and deep inside rocks within the earth's crust. Such habitats are lived in by extremophiles.

In the context of the present invention microorganisms do not include live yeast.

Lactic Acid Bacteria (or Lactobacillales) are an order of Gram-positive, low-GC (low guanine-cytosine content), acid-tolerant, generally nonsporulating, non-respiring, either rod or coccus-shaped bacteria that share common metabolic and physiological characteristics. These bacteria, usually found in decomposing plants and milk products, produce lactic acid as the major metabolic end product of carbohydrate bio-conversion. The lactic acid bacteria are genera of microorganism which produce organic acids, such as lactic acid and acetic acid, as metabolic products of carbohydrate bio-conversion. The genera are in particular, but are not limited to, *Lactobacillus, Pediococcus, Lactococcus, Enterococcus, Weisella, Streptococcus*, and *Leuconostoc*.

Other Genera

In the context of the present invention, other genera refer to the most relevant other bacterial genera in relation to the invention. They comprise a number of genera which also produce organic acids, such as lactic acid and acetic acid, as metabolic products of carbohydrate bio-conversion, but often to a lesser extent than the lactic acid bacteria.

In the context of the present invention other genera than the lactic acid comprises, but are not limited to, *Bacillus, Bifidobacterium, Brevibacillus, Propionibacterium, Clostridium*, and *Geobacillus*.

*Bacillus* are genera in the order of Bacillales. The bacteria are gram-positive, rod-shaped, and form endospores under stressful conditions. Certain strains are used as probiotics.

Processing Aids:

1. Enzymes

Enzyme(s) is a very large class of protein substances with the ability to act as catalysts. Commonly, they are divided in six classes, and the main classes falling within the scope of this invention can be transferases that transfer functional groups or hydrolases that hydrolyze various bonds. Typical examples can comprise: protease(s), peptidase(s), (α-)galactosidase(s), amylase(s), glucanase(s), pectinase(s), hemicellulase(s), phytase(s), lipase(s), phospholipase(s), transferase(s), cellulase(s), and oxido-reductase(s).

2. Plant Components and Organic Processing Agents

Some of the functional properties that are important in this context are: Antioxidant, anti-bacterial action, wetting properties and stimulation of enzyme activity.

The list of plant-based components is huge, but the most important are the following: Rosemary, thyme, oregano, flavonoids, phenolic acids, saponins, and α- and β-acids from hops e.g. α-lupulic acid for the modulation of soluble carbohydrates.

Furthermore, organic acids e.g. sorbic-, propionic-, lactic-, citric-, and ascorbic acid, and their salts for the adjustment of the pH-value, preservation and chelating properties is part of this group of processing aids.

3. Inorganic Processing Agents

Comprise inorganic compositions for example anticaking and flow improving agents in the final product e.g. potassium aluminium silicate, etc.

Comprise inorganic acids e.g. hydrochloric acid.

Processed Food Products:

Comprise dairy products, processed meat products, sweets, desserts, ice cream desserts, canned products, freeze dried meals, dressings, soups, convenience food, bread, cakes, etc.

Processed Feed Products:

Comprise ready-to-use feed for animals such as piglets, calves, poultry, furred animals, sheep, cats, dogs, fish, and crustaceans, etc.

Pharmaceutical Products:

Comprise products, typically in the form of a tablet or in granulated form, containing one or more biologically active ingredients intended for curing and/or alleviating the symptoms of a disease or a condition. Pharmaceutical products furthermore comprise pharmaceutically acceptable excipients and/or carriers. The solid bio products herein disclosed are very well suited for use as a pharmaceutically acceptable ingredient in a tablet or granulate.

Cosmetic Products:

Comprise products intended for personal hygiene as well as improved appearance such as conditioners and bath preparations.

DETAILED DESCRIPTION OF THE INVENTION

In a first embodiment of the method of the invention at least 20% by weight of the biomass, such as at least 30%, at least 40%, at least 50%, at least 60%, at least 70%, at least 80%, or at least 90% by weight, comprises proteinaceous matter originating from optionally defatted soya. The soya may also be dehulled.

In a second embodiment of the method of the invention at least 20% by weight of the biomass, such as at least 30%, at least 40%, at least 50%, at least 60%, at least 70%, at least 80%, or at least 90% by weight, comprises proteinaceous matter originating from optionally defatted rape seeds.

In a third embodiment of the method of the invention the biomass comprises proteinaceous matter originating from optionally defatted soya in an amount of from 5% to 95% by weight in mixture with proteinaceous matter originating from optionally defatted rape seed in an amount of from 95% to 5% by weight optionally in further mixture with proteinaceous matter originating from fava beans, peas, sunflower seeds and/or cereals in amounts to make up a total amount of the proteinaceous matter of 100% by weight.

In any of the embodiments of the invention the biomass comprising proteinaceous matter may further comprise oligosaccharides, and/or polysaccharides, and/or further comprises oils and fats, e.g. from seeds of oil bearing plants.

In any of the embodiments of the invention the solid transformation product of the substrate may be a product of the transformation of carbohydrates, in particular oligosaccharides and polysaccharides, and/or proteinaceous matter originating from said biomass, such as a transformation product of pulses, such as soya, pea, lupine, sunflower, and/or cereals, such as wheat, or maize, or from seeds of oil bearing plants, e.g. rape seed.

In any of the embodiments of the invention the live microorganism or mixture of live microorganisms may be one or more microorganisms which can produce one or more organic compounds, such as organic acids, e.g. formic acid, acetic acid, propionic acid, butyric acid, lactic acid, and succinic acid, or alcohols, e.g. ethanol, from carbohydrates.

In any of the embodiments of the invention the live microorganism or combination of live microorganisms may be one or more organic acid producing microorganism(s).

In any of the embodiments of the invention the live microorganism or combination of live microorganisms may be selected from the following list of genera:

Lactobacillus
Lactococcus
Streptococcus
Pediococcus
Enterococcus
Leuconostoc
Weisella
Bifidobacterium
Bacillus
Brevibacillus
Propionibacterium
Clostridium
Trichoderma
Candida
Aspergillus.

In any of the embodiments of the invention the live microorganism or combination of live microorganisms may be selected from Lactobacillus strains, and the mixture may be incubated at a temperature of 15-50° C.

In any of the embodiments of the invention the live microorganism or combination of live microorganisms may be selected from Lactobacillus, Pediococcus, Enterococcus, Lactococcus, Streptococcus, and Weisella strains, and the mixture may be incubated at a temperature of 15-50° C.

In any of the embodiments of the invention the live microorganism or combination of live microorganisms may be selected from Bacillus strains, and the mixture may be incubated a temperature of 20-60° C.

In any of the embodiments of the invention the live microorganism or combination of live microorganisms may be selected from Bifidobacterium strains, and the mixture may be incubated at a temperature of 20-45° C.

In any of the above embodiments water is added to said substrate of biomass in an amount which provides an initial incubation mixture having a ratio of wet bulk density to dry bulk density from 0.65 to 1.40, such as 0.70, 0.75, 0.80, 0.85, 0.90, 0.95, 1.00, 1.10, 1.15, 1.20, 1.25, 1.30, or 1.35.

In any of the above embodiments the live microorganism or combination of live microorganisms is used in an amount of $10^3$ to $10^{11}$ CFU (colony forming units) per g of said substrate of biomass, such as $10^3$, $10^4$, $10^5$, $10^6$, $10^7$, $10^8$, $10^9$, or $10^{10}$ CFU/g substrate of biomass. The skilled person would now how to select a suitable amount, depending on the selected process conditions, such as reactor dimension, the process time and temperature, the applied microorganism, and the transformation product to be produced.

In any of the embodiments of the invention water is added to the substrate in an amount to provide a ratio of wet bulk density to dry bulk density from about 0.60 to 1.45 in the substrate, such as from about 0.65 to about 1.40, e.g. 0.70, 0.75, 0.80, 0.85, 0.90, 0.95, 1.00, 1.10, 1.15, 1.20, 1.25, 1.30, or 1.35.

In any of the embodiments of the invention at least 40% by weight of the biomass, such as at least 50%, at least 60%, at least 70%, at least 80% or at least 90% by weight, may comprise proteinaceous matter originating from optionally defatted rape seeds, whereas water may be added to the substrate in an amount to provide a ratio of wet bulk density to dry bulk density from about 0.65 to about 1.10, such as 0.75, 0.80, 0.85, 0.90, 0.95, 1.00, or 1.05.

In any of the embodiments of the invention one or more processing aids selected from enzymes, plant components, and organic and inorganic processing agents may be added to the substrate of biomass and/or to the initial incubation mixture.

In any of the embodiments of the invention the filling degree of said incubation tank may be kept constant. This will result in a uniform flow.

In any of the embodiments of the invention a processing aid selected as α-galactosidase may be added to the substrate of biomass and/or to the initial incubation mixture, e.g. an α-galactosidase preparation is added to the substrate of biomass and/or to the initial incubation mixture in an amount of from 0.05 to 50 α-galactosidase units pr. g. dry matter of substrate of biomass, such as from 0.5 to 25 α-galactosidase units pr. g. dry matter of substrate of biomass, e.g. from 1 to 10, from 2 to 8, from 3 to 6, or from 4 to 5 α-galactosidase units pr. g. dry matter of substrate of biomass.

In any of the embodiments of the invention the incubation can be carried out under anaerobic conditions. The anaerobic conditions are facilitated by the present invention.

In any of the embodiments of the invention the water content in the incubation mixture may be from 35% to 70% by weight, such as 40%, 45%, 50%, 55%, 60%, or 65% by weight. Thus, the water content in the initial mixture does not exceed 70% by weight and it may vary from e.g. from 40% to 65%, from 45% to 60%, from 48% to 52%, or 50% to 55%, such as 49, 50, 51, 52, 53, or 54%.

In any of the embodiments of the invention the mixture is incubated for 1-240 hours at 15-70° C. The skilled will know how to optimise the reaction time and the reaction temperature in view of the other reaction conditions, such as the selection of microorganisms. Thus, the temperature may vary as e.g. 20-65° C., 25-60° C., 30-55° C., 35-50° C., or 40-45° C.; and the reaction time may be selected as e.g. 2 to 180 hours, such as 5 to 150 hours, 7 to 120 hours, 10 to 80 hours, 20 to 60 hours, or 28 to 48 hours, at each and every one of the here mentioned temperature intervals.

In any of the embodiments of the invention the solid transformation product of the substrate may by dried, optionally followed by milling.

In any of the embodiments of the invention the substrate mixture may be incubated at a time and a temperature sufficient to inactivate the microorganisms, anti-nutritional factors and the enzyme(s) if used partly or totally, and if desired.

In any of the embodiments of the invention the non-agitated incubation tank may be closed.

In any of the embodiments of the invention the non-agitated incubation tank can be of a vertical, oblong cylindrical or polyhedral type. The advantage of using this type is that it is space-saving and as it is non-agitated the operating costs and maintenance costs for mixing equipment are avoided.

In any of the embodiments of the invention the area in the upper part of said non-agitated incubation tank may be less than the area in the lower part i.e. the tank is of conical shape. The advantage of this is that the slip effect is increased so that biomasses with a reduced flowability can be used.

In any of the embodiments of the invention the non-agitated incubation tank may have insulating matting or a thermal dimple jacket and means to control the temperature inside the incubation tank.

The solid transformation product of the substrate provided by the invention may be dried to a water content of not more than 15%, 13%, 10%, 6%, 4%, or 2% by weight and optionally be in milled form.

The solid product of the invention can be a product of the transformation of proteinaceous matter and/or carbohydrates originating from said biomass. The solid transformation product may have reduced content of anti-nutritional factors, such as trypsin inhibitors, antigens, flatulence-producing oligosaccharides, e.g. stachyose and raffinose; phytic acid, and lectin.

The solid product of the invention may comprise at least 40% proteinaceous matter by weight of dry matter originating from soya.

The solid product of the invention may comprise at least 40% proteinaceous matter by weight of dry matter originating from rape seed.

The solid product of the invention may comprise proteins in an amount of 30-65% by weight on dry matter basis originating from plant parts of soya, rape seed, or sun flower, or mixtures thereof.

Finally, the invention provides a food, feed, cosmetic or pharmaceutical product or a nutritional supplement containing from 1% to 99% by weight of a solid transformation product produced according to the invention.

EXAMPLES

Density Ratio

Example 1

Ratio of Wet Bulk Density/Dry Bulk Density for Preferred Substrates Based on Various Biomasses 1.1 Biomasses Used in the Procedure:

Soya

The soya used was defatted Soya Bean Meal (SBM).

Maize

The maize used was whole maize, ground on a hammer mill through a 3.5 mm sieve.

Wheat

The wheat used was whole wheat, ground on a hammer mill through a 3.5 mm sieve.

Sunflower

The sunflower used was defatted Sunflower Seed Meal (SSM).

Rapeseed

The rapeseed used was defatted Rape Seed Meal (RSM).

Fava Beans

The beans used were whole fava beans.

Pea Protein

The pea protein used was a pea protein concentrate.

1.2 Description of the Procedure:

The amount(s) of biomass and water tabulated in the following was mixed for ten minutes followed by fifty minutes of equilibration in a closed container.

After this the material was poured into a measuring cup of 500 mL and its mass determined by weighing the cup and subtracting the tare of the cup.

The bulk density was calculated as mass/untapped volume in $kg/m^3$.

The dry bulk density used was the measured bulk density of the biomass without addition of water.

The wet bulk density was the bulk density of the biomass with added water.

The ratio was calculated as wet bulk density divided by the dry bulk density.

The moisture content of the biomasses was determined by drying to constant weight.

After addition of water the moisture in the mixture was determined by calculation.

1.3 Results:

The results for 100% soya and 80% mixtures with soya are tabulated in the following:

| Soya | Maize | Wheat | Sunflower | Rapeseed | Fava bean | Pea | Water In g | Moisture In % | Bulk Density $kg/m^3$ | Ratio |
|---|---|---|---|---|---|---|---|---|---|---|
| 1000 g | | | | | | | 0 | 10.9 | 665 | — |
| 1000 g | | | | | | | 100 | 19.0 | 638 | 0.96 |
| 1000 g | | | | | | | 250 | 28.7 | 500 | 0.75 |

-continued

| Soya | Maize | Wheat | Sunflower | Rapeseed | Fava bean | Pea | Water In g | Moisture In % | Bulk Density kg/m³ | Ratio |
|---|---|---|---|---|---|---|---|---|---|---|
| 1000 g | | | | | | | 450 | 38.6 | 476 | 0.72 |
| 1000 g | | | | | | | 750 | 49.1 | 470 | 0.71 |
| 1000 g | | | | | | | 900 | 53.1 | 572 | 0.86 |
| 1000 g | | | | | | | 1100 | 57.6 | 655 | 0.98 |
| 1000 g | | | | | | | 1400 | 62.9 | 715 | 1.07 |
| 1000 g | | | | | | | 1900 | 69.3 | 889 | 1.34 |
| 800 g | 200 g | | | | | | 0 | 11.4 | 703 | — |
| 800 g | 200 g | | | | | | 450 | 38.9 | 617 | 0.88 |
| 800 g | 200 g | | | | | | 900 | 53.4 | 634 | 0.90 |
| 800 g | 200 g | | | | | | 1900 | 69.4 | 1008 | 1.43 |
| 800 g | | 200 g | | | | | 0 | 11.7 | 694 | — |
| 800 g | | 200 g | | | | | 450 | 39.1 | 580 | 0.84 |
| 800 g | | 200 g | | | | | 900 | 53.5 | 623 | 0.90 |
| 800 g | | 200 g | | | | | 1900 | 69.5 | 960 | 1.38 |
| 800 g | | | 200 g | | | | 0 | 10.4 | 683 | — |
| 800 g | | | 200 g | | | | 450 | 38.2 | 554 | 0.81 |
| 800 g | | | 200 g | | | | 900 | 52.9 | 598 | 0.88 |
| 800 g | | | 200 g | | | | 1900 | 69.1 | 926 | 1.36 |
| 800 g | | | | 200 g | | | 0 | 11.3 | 711 | — |
| 800 g | | | | 200 g | | | 100 | 19.4 | 576 | 0.81 |
| 800 g | | | | 200 g | | | 250 | 29.0 | 514 | 0.72 |
| 800 g | | | | 200 g | | | 450 | 38.8 | 483 | 0.68 |
| 800 g | | | | 200 g | | | 750 | 49.3 | 490 | 0.69 |
| 800 g | | | | 200 g | | | 900 | 53.3 | 597 | 0.84 |
| 800 g | | | | 200 g | | | 1100 | 57.8 | 528 | 0.74 |
| 800 g | | | | 200 g | | | 1900 | 69.4 | 908 | 1.28 |
| 800 g | | | | | 200 g | | 0 | 11.1 | 691 | — |
| 800 g | | | | | 200 g | | 450 | 38.7 | 569 | 0.82 |
| 800 g | | | | | 200 g | | 900 | 53.2 | 605 | 0.88 |
| 800 g | | | | | 200 g | | 1900 | 69.3 | 941 | 1.36 |
| 800 g | | | | | | 200 g | 0 | 11.2 | 703 | — |
| 800 g | | | | | | 200 g | 450 | 38.7 | 488 | 0.69 |
| 800 g | | | | | | 200 g | 900 | 53.2 | 728 | 1.04 |
| 800 g | | | | | | 200 g | 1900 | 69.4 | 964 | 1.37 |

The results for 60% and 40% of soya mixtures with maize, sunflower and rapeseed as well as 100% rapeseed are tabulated in the following:

| Soya | Maize | Sunflower | Rapeseed | Water | Moisture In % | Bulk Density kg/m³ | Ratio |
|---|---|---|---|---|---|---|---|
| 600 g | 400 g | | | 0 g | 11.8 | 703 | — |
| 600 g | 400 g | | | 250 g | 29.5 | 651 | 0.93 |
| 600 g | 400 g | | | 450 g | 39.2 | 626 | 0.89 |
| 600 g | 400 g | | | 750 g | 49.6 | 631 | 0.90 |
| 600 g | 400 g | | | 900 g | 53.6 | 666 | 0.95 |
| 600 g | 400 g | | | 1100 g | 58.0 | 723 | 1.03 |
| 600 g | 400 g | | | 1400 g | 63.3 | 796 | 1.13 |
| 600 g | | 400 g | | 0 g | 10.0 | 644 | — |
| 600 g | | 400 g | | 100 g | 18.2 | 530 | 0.82 |
| 600 g | | 400 g | | 250 g | 28.0 | 435 | 0.68 |
| 600 g | | 400 g | | 450 g | 37.9 | 433 | 0.67 |
| 600 g | | 400 g | | 750 g | 48.6 | 436 | 0.68 |
| 600 g | | 400 g | | 900 g | 52.6 | 480 | 0.75 |
| 600 g | | 400 g | | 1100 g | 57.1 | 449 | 0.70 |
| 600 g | | 400 g | | 1400 g | 62.5 | 616 | 0.96 |
| 600 g | | | 400 g | 0 g | 11.7 | 643 | — |
| 600 g | | | 400 g | 100 g | 19.7 | 560 | 0.82 |
| 600 g | | | 400 g | 250 g | 29.4 | 502 | 0.78 |
| 600 g | | | 400 g | 450 g | 39.1 | 503 | 0.78 |
| 600 g | | | 400 g | 750 g | 49.5 | 492 | 0.77 |
| 600 g | | | 400 g | 900 g | 53.5 | 516 | 0.80 |
| 600 g | | | 400 g | 1100 g | 57.9 | 545 | 0.85 |
| 600 g | | | 400 g | 1400 g | 63.2 | 655 | 1.02 |
| 400 g | 600 g | | | 0 g | 12.3 | 718 | — |
| 400 g | 600 g | | | 250 g | 29.9 | 636 | 0.89 |
| 400 g | 600 g | | | 450 g | 39.5 | 638 | 0.89 |
| 400 g | 600 g | | | 750 g | 49.9 | 666 | 0.93 |
| 400 g | 600 g | | | 900 g | 53.8 | 721 | 1.00 |
| 400 g | 600 g | | | 1100 g | 58.2 | 802 | 1.12 |

-continued

| Soya | Maize | Sunflower | Rapeseed | Water | Moisture In % | Bulk Density kg/m³ | Ratio |
|---|---|---|---|---|---|---|---|
| 400 g | 600 g | | | 1400 g | 63.5 | 988 | 1.38 |
| 400 g | | 600 g | | 0 g | 9.5 | 654 | — |
| 400 g | | 600 g | | 100 g | 17.7 | 535 | 0.82 |
| 400 g | | 600 g | | 250 g | 27.6 | 422 | 0.65 |
| 400 g | | 600 g | | 450 g | 37.6 | 487 | 0.74 |
| 400 g | | 600 g | | 750 g | 48.3 | 491 | 0.75 |
| 400 g | | 600 g | | 900 g | 52.4 | 512 | 0.78 |
| 400 g | | 600 g | | 1100 g | 56.9 | 585 | 0.89 |
| 400 g | | 600 g | | 1400 g | 62.3 | 612 | 0.94 |
| 400 g | | | 600 g | 0 g | 12.1 | 658 | — |
| 400 g | | | 600 g | 100 g | 20.1 | 556 | 0.84 |
| 400 g | | | 600 g | 250 g | 29.7 | 471 | 0.72 |
| 400 g | | | 600 g | 450 g | 39.4 | 458 | 0.70 |
| 400 g | | | 600 g | 750 g | 49.8 | 486 | 0.74 |
| 400 g | | | 600 g | 900 g | 53.7 | 486 | 0.74 |
| 400 g | | | 600 g | 1100 g | 58.1 | 531 | 0.81 |
| 400 g | | | 600 g | 1400 g | 63.4 | 605 | 0.92 |
| 0 g | | | 1000 g | 0 g | 12.9 | 616 | — |
| 0 g | | | 1000 g | 100 g | 20.8 | 484 | 0.79 |
| 0 g | | | 1000 g | 250 g | 30.3 | 438 | 0.71 |
| 0 g | | | 1000 g | 450 g | 39.9 | 457 | 0.74 |
| 0 g | | | 1000 g | 750 g | 50.2 | 507 | 0.82 |
| 0 g | | | 1000 g | 900 g | 54.1 | 535 | 0.87 |
| 0 g | | | 1000 g | 1100 g | 58.5 | 585 | 0.95 |
| 0 g | | | 1000 g | 1400 g | 63.7 | 688 | 1.12 |

Example 2

Ratio of Wet Bulk Density/Dry Bulk Density for Substrates Based on Various Biomasses and Used in Experiments with Various Microorgansims The determination of bulk density was performed by pouring an amount of material (approx. 250 ml) in a 250 ml measuring cylinder and reading the volume after leveling the surface by gently shaking the cylinder. Following this, the weight of the material was determined. Dry bulk densities and wet bulk densities were done in triplicates.

The results are summarised in the following table:

| Biomass | Dry matter in % by weight | Density ratio = wet bulk density/ dry bulk density |
|---|---|---|
| 100% SBM | 35 | 1.13 |
| 100% SBM | 40 | 0.95 |
| 100% SBM | 42.5 | 0.86 |
| 100% SBM | 52 | 0.85 |
| 100% SBM | 55 | 0.84 |
| 80% SBM + 20% RSM | 35 | 1.05 |
| 80% SBM + 20% RSM | 42.5 | 0.88 |
| 80% SBM + 20% RSM | 52 | 0.78 |
| 60% SBM + 40% SSM | 35 | 0.94 |
| 60% SBM + 40% SSM | 42.5 | 0.84 |
| 60% SBM + 40% SSM | 52 | 0.73 |

Lab-Scale Incubation Tests of New Technology Method

The following examples 3 to 9 were lab scale experiments conducted under the following conditions:

Background:

The background for the following lab-scale incubation tests was to imitate the conditions in the method of the present invention.

Materials and Methods:

Materials

Biomasses: Soya Bean Meal (SBM), Rape Seed Meal (RSM) and Sunflower Seed Meal (SSM) —as described in section 1.1.

Water: Normal tap water

Microorganisms: The microorganism(s) used are specified for each example. For all experiments, unless indicated in the specific example, microorganisms were dosed with approximately $10^8$ CFU/g DM. Lactic acid bacteria and Bifidobacteria were grown in MRS broth, washed in 0.9% NaCl, and dosed to the incubation based on a relationship between $OD_{600}$ and CFU/ml. The ml amount needed to dose $10^8$ CFU/g DM was subtracted from the total water amount stated under each example. For the Bacillus strains, most of them were dosed as dry formulated cultures, but Geobacillus denitrificans and Bacillus smithii were grown in Nutrient Broth, and washed in the same way, and dosed in the same way, as described for the Lactic acid bacteria strains.

The microorganisms and their origin used in the examples are shown in the following table:

| Strain | Origin |
|---|---|
| Lactobacillus plantarum | Pangoo |
| Lactobacillus paracasei 5622 | DSMZ |
| Lactobacillus fermentum | Bio Growing |
| Lactobacillus acidophilus | Bio Growing |
| Lactobacillus delbruckii bulgaricus | Bio Growing |
| Lactobacillus debruckii sunkii 24966 | DSMZ |
| Lactobacillus farci minis | Own isolate |
| Lactobacillus formosensis | Own isolate |
| Lactobacillus salivarius 20554 | DSMZ |
| Bacillus coagulans | Pangoo |
| Bacillus licheniformis | BioCat |

| Strain | Origin |
|---|---|
| *Bacillus subtilis* | BioCat |
| *Bacillus smithii* 2319 | DSMZ |
| *Lactococcus lactis* | Bio Growing |
| *Bifidobacterium animalis* | Bio Growing |
| *Pediococcus acidolactici* | Pangoo |
| *Enterococcus faecium* | Pangoo |
| *Enterococcus faecalis* | Pangoo |
| *Enterococcus durans* | Own isolate |
| *Weisella hellenica* | Own isolate |
| *Streptococcus thermophiles* | Bio Growing |
| *Geobacillus thermodenitrificans* 466 | DSMZ |

DSMZ: Deutsche Sammlung von Mikroorganismen und Zellkulturen

Processing aid: α-galactosidase from Bio-Cat (12,500 U/g). The α-galactosidase was dosed in 1 ml water, which was substrated from the total addition of water stated in the table of each example.

Experimental Method Used

Incubation Tank:

To imitate bio-conversion conditions where oxygen become non-available, bio-conversion where performed in strong plastic bags, squeezed by hand to remove air and closed tightly with a strap, still allowing $CO_2$ to escape.

Incubation:

Samples were incubated at different temperatures, different water contents and at different length in time, specified for each example. The incubation was stopped by heating 100° C. for 30 min.

Analytical Methods:

Acid Analysis:

The analysis was conducted by LUFA Oldenburg, Germany, using an aqueous digestion with membrane filtration and subsequent measurement by an ion chromatograph.

Sucrose and Galactose (Sugars):

The content of sucrose and galactose was determined by thin-layer chromatography.

Stationary phase—Silica gel 60 (Merck 1.05553.0001)

Mobile phase—120 mL n-butanol, 80 mL pyridine and 60 mL demineralized water

Spots are visualized with a liquid composed of 8 g diphenylamine, 335 mL acetone 8 mL aniline and 60 mL phosphoric acid.

Sugar concentrations were determined by comparison with known standards.

pH:

pH was measured in 10% DM dilutions with a HQ 411d from HACH.

CFU:

CFU were determined by plate spreading, using MRS agar plates for lactic acid bacteria, and Nutrient agar for the *Bacillus* strains.

Example 3

Testing Different Production Organisms (LAB) at 20° C., at Different Dry Matter Ratios Experimental Set-Up:

| Strain | Dry matter % of weight | Inoculation level CFU/g DM | SBM (88% DM) g | α-galactosidase mg | Water Ml |
|---|---|---|---|---|---|
| *Lactobacillus salivarius* | 42.5 | $1*10^8$ | 113.6 | 120 | 122 |
| *Lactobacillus debruckii sunkii* | 42.5 | $1*10^8$ | 113.6 | 120 | 122 |
| *Lactobacillus plantarum* | 35 | $1*10^8$ | 113.6 | 120 | 172 |
| *Lactobacillus plantarum* | 42.5 | $1*10^8$ | 113.6 | 120 | 122 |
| *Lactobacillus plantarum* | 52 | $1*10^8$ | 113.6 | 120 | 79 |
| *Lactobacillus paracasei* | 35 | $1*10^8$ | 113.6 | 120 | 172 |
| *Lactobacillus paracasei* | 42.5 | $1*10^8$ | 113.6 | 120 | 122 |

Samples were incubated in a 20° C. thermostatic water bath.

Results:

After 44 hours of incubation the following results were obtained, showing growth, sugar conversion and acid production:

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| *Lactobacillus plantarum* | 35 | 4.9 | 1.2 | 6.1 | 4.9 | $3*10^{10}$ | 0 | 0 |
| *Lactobacillus plantarum* | 42.5 | 3.7 | 1.3 | 5.0 | 5.2 | $2*10^{10}$ | 0 | 0 |
| *Lactobacillus Plantarum* | 52 | 3.2 | 0.9 | 4.1 | 5.2 | $2*10^{10}$ | 0 | 0 |

After 116 hours of incubation the following results were obtained, showing growth, sugar conversion and acid production:

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| Lactobacillus salivarius | 42.5 | 3.4 | 1.0 | 4.4 | 4.9 | $9.5*10^9$ | 0.5 | 1.6 |
| Lactobacillus debruckii sunkii | 42.5 | 3.7 | 0.5 | 4.2 | 4.9 | $3.9*10^9$ | 0 | 1.6 |
| Lactobacillus plantarum | 35 | 7.3 | 1.1 | 8.4 | 4.5 | $2.0*10^{10}$ | 0 | 0 |
| Lactobacillus plantarum | 42.5 | 5.7 | 1.1 | 6.8 | 4.7 | $2.3*10^{10}$ | 0 | 0 |
| Lactobacillus plantarum | 52 | 5.1 | 1.2 | 6.3 | 4.8 | $2.2*10^{10}$ | 0 | 0 |
| Lactobacillus paracasei | 35 | 4.7 | 0.8 | 5.5 | 4.8 | $1.9*10^{10}$ | 6 | 0 |
| Lactobacillus paracasei | 42.5 | 3.2 | 0.6 | 3.8 | 4.8 | $1.8*10^{10}$ | 6 | 0 |

Part of the sugars was still bound in oligosaccharides in this experiment, even after 166 hours. The potential for acid production is thereby larger than obtained in this test.

Example 4

Testing Different Production Organisms (LAB) at 30° C., at 40% DM

Experimental Set-Up:

| Strain | Dry matter % of weight | Inoculation level CFU/g DM | SBM (88% DM) G | α-galactosidase mg | Water Ml |
|---|---|---|---|---|---|
| Lactobacillus plantarum | 40 | $1*10^8$ | 68.2 | 72 | 82 |
| Lactococcus lactis | 40 | $1*10^8$ | 68.2 | 72 | 82 |
| Enterococcus faecium | 40 | $1*10^8$ | 68.2 | 72 | 82 |

Samples were incubated in a 30° C. thermostatic water bath.

Results:

After 45 hours of incubation the following results were obtained, showing growth, sugar conversion and acid production:

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| Lactobacillus plantarum | 40 | 6.2 | 1.1 | 7.3 | 4.6 | $1*10^{10}$ | 0 | 1.4 |
| Lactococcus lactis | 40 | 3.7 | 0.9 | 4.6 | 4.8 | $1*10^{10}$ | 1.8 | 1.8 |
| Enterococcus faecium | 40 | 5.1 | 1.4 | 6.5 | 4.8 | $2*10^{10}$ | 0.4 | 1.4 |

After 69 hours of incubation the following results were obtained, showing sugar conversion and acid production (CFU not determined):

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| Lactobacillus plantarum | 40 | 7.0 | 1.0 | 8.0 | 4.5 | | 0 | 0.5 |
| Lactococcus lactis | 40 | 4.3 | 1.2 | 5.5 | 4.6 | | 1.8 | 1.2 |
| Enterococcus faecium | 40 | 5.8 | 1.3 | 7.1 | 4.6 | | 0 | 0.6 |

Example 5

Testing Different Production Organisms at 37° C., at Different Dry Matter Ratios
Experimental Set-Up:

| Strain | Exp. No. | Dry matter % of weight | Inoculation level CFU/g DM | SBM (88% DM) | α-galactosidase mg | Water Ml |
|---|---|---|---|---|---|---|
| Lactobacillus plantarum | 1 | 35 | $1*10^8$ | 113.6 | 120 | 172 |
| Lactobacillus plantarum | 2 | 42.5 | $1*10^8$ | 113.6 | 120 | 122 |
| Lactobacillus plantarum | 3 | 42.5 | $1*10^8$ | 113.6 | Not added | 122 |
| Lactobacillus plantarum | 4 | 42.5 | $1*10^7$ | 68.2 | 72 | 73 |
| Lactobacillus plantarum | 5 | 42.5 | $1*10^9$ | 68.2 | 72 | 73 |
| Lactobacillus plantarum | 6 | 52 | $1*10^8$ | 113.6 | 120 | 79 |
| Lactobacillus paracasei | 7 | 35 | $1*10^8$ | 113.6 | 120 | 172 |
| Lactobacillus paracasei | 8 | 42.5 | $1*10^8$ | 113.6 | 120 | 122 |
| Lactobacillus paracasei | 9 | 52 | $1*10^8$ | 113.6 | 120 | 79 |
| Bacillus coagulans | 10 | 35 | $1*10^8$ | 68.2 | 72 | 103 |
| Bacillus coagulans | 11 | 42.5 | $1*10^8$ | 68.2 | 72 | 73 |
| Bacillus coagulans | 12 | 42.5 | $1*10^8$ | 113.6 | Not added | 122 |
| Bacillus coagulans | 13 | 42.5 | $1*10^7$ | 68.2 | 72 | 73 |
| Bacillus coagulans | 14 | 55 | $1*10^8$ | 68.2 | 72 | 41 |
| Bacillus licheniformis | 15 | 35 | $1*10^8$ | 68.2 | 72 | 103 |
| Bacillus licheniformis | 16 | 42.5 | $1*10^8$ | 68.2 | 72 | 73 |
| Bacillus licheniformis | 17 | 55 | $1*10^8$ | 68.2 | 72 | 41 |
| Bacillus subtilis | 18 | 35 | $1*10^8$ | 68.2 | 72 | 103 |
| Bacillus subtilis | 19 | 42.5 | $1*10^8$ | 113.6 | 120 | 122 |
| Bacillus subtilis | 20 | 55 | $1*10^8$ | 68.2 | 72 | 41 |
| Lactobacillus fermentum | 21 | 42.5 | $1*10^8$ | 68.2 | 72 | 73 |
| Lactobacillus acidophilus | 22 | 42.5 | $6*10^7$ | 68.2 | 72 | 73 |
| Lactobacillus delbruckii bulgaricus | 23 | 42.5 | $2*10^7$ | 68.2 | 72 | 73 |
| Lactobacillus farciminis | 24 | 42.5 | $6*10^6$ | 68.2 | 72 | 73 |
| Lactobacillus formosensis | 25 | 42.5 | $1*10^8$ | 113.6 | 120 | 122 |

-continued

| Strain | Exp. No. | Dry matter % of weight | Inoculation level CFU/g DM | SBM (88% DM) | α-galactosidase mg | Water Ml |
|---|---|---|---|---|---|---|
| Lactococcus lactis | 26 | 42.5 | $4*10^7$ | 68.2 | 72 | 73 |
| Bifidobacterium animalis | 27 | 42.5 | $1*10^8$ | 68.2 | 72 | 73 |
| Pediococcus acidolactici | 28 | 42.5 | $1*10^8$ | 68.2 | 72 | 73 |
| Enterococcus faecium | 29 | 42.5 | $1*10^8$ | 68.2 | 72 | 73 |
| Enterococcus faecalis | 30 | 42.5 | $1*10^8$ | 68.2 | 72 | 73 |
| Enterococcus durans | 31 | 42.5 | $1*10^8$ | 113.6 | 120 | 122 |
| Weisella hellenica | 32 | 42.5 | $1*10^8$ | 113.6 | 120 | 122 |
| Lactobacillus salivarius + Lactobacillus paracasei | 33 | 42.5 | $1*10^8$ and $3*10^7$ | 113.6 | 120 | 122 |
| Streptococcus thermophilus + Bifidobacterium animalis | 34 | 42.5 | $5*10^7$ and $5*10^7$ | 113.6 | 120 | 122 |
| Pediococcus acidolactici + Lactobacillus plantarum | 35 | 42.5 | $5*10^7$ and $5*10^7$ | 113.6 | 120 | 122 |
| Lactobacillus farciminis + Lactobacillus plantarum | 36 | 42.5 | $5*10^7$ and $5*10^7$ | 113.6 | 120 | 122 |
| Lactobacillus plantarum + sucrose (5% of DM) | 37 | 42.5 | $1*10^8$ | 113.6 | 120 | 122 |

Results:

After 18.5 to 20 hours of incubation the following results were obtained, showing growth, sugar conversion and acid production

| Strain | Exp No. | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|---|
| Lactobacillus plantarum | 1 | 35 | 6.1 | 1.2 | 7.3 | 4.6 | nd | 1 | 2 |
| Lactobacillus plantarum Inoc: $10^8$ CFU/g | 2 | 42.5 | 5.3 | 1.2 | 6.5 | 4.7 | nd | 1 | 2 |
| Lactobacillus plantarum Inoc: $10^7$ CFU/g | 4 | 42.5 | 5.5 | 1.2 | 6.7 | 5.0 | nd | 2 | 2 |
| Lactobacillus plantarum Inoc: $10^9$ CFU/g | 5 | 42.5 | 6.5 | 1.2 | 7.7 | 4.8 | nd | 1 | 2 |
| Lactobacillus plantarum | 6 | 52 | 4.7 | 1.1 | 5.8 | 4.8 | nd | 2 | 2 |
| Lactobacillus paracasei | 7 | 35 | 5.3 | 0.1 | 5.4 | 4.4 | nd | 2 | 2 |
| Lactobacillus paracasei | 8 | 42.5 | 4.5 | 0.1 | 4.6 | 4.5 | nd | 2.6 | 2 |
| Bacillus coagulans Inoc: $10^8$ CFU/g | 11 | 42.5 | 4.5 | 1.4 | 5.9 | 5.3 | $8*10^9$ | 2.5 | 2 |
| Bacillus coagulans Inoc: $10^7$ CFU/g | 13 | 42.5 | 3.6 | 1.4 | 5.0 | 5.4 | $7*10^9$ | 2.5 | 2 |

-continued

| Strain | Exp No. | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|---|
| Lactobacillus farciminis (no 1) | 24 | 42.5 | 4.2 | 0.1 | 4.3 | 4.8 | nd | 4 | 3.5 |
| Lactococcus lactis | 26 | 42.5 | 3.0 | 2.0 | 5.0 | 5.0 | nd | 2 | 2 |
| Bifidobacterium animalis | 27 | 42.5 | 4.1 | 2.0 | 6.1 | 5.0 | nd | 2 | 2 |
| Pediococcus acidolactici | 28 | 42.5 | 3.7 | 1.5 | 5.2 | 5.1 | nd | 2 | 2 |
| Enterococcus faecium | 29 | 42.5 | 5.4 | 1.4 | 6.8 | 5.1 | nd | 2 | 2 |
| Lactobacillus salivarius + Lactobacillus paracasei | 33 | 42.5 | 5.1 | 0.1 | 5.2 | 4.4 | nd | 2 | 2 |
| Streptococcus thermophiles + Bifidobacterium animalis | 34 | 42.5 | 4.1 | 1.9 | 6.0 | 4.9 | nd | 2 | 2 |
| Pediococcus acidolactici + Lactobacillus plantarum | 35 | 42.5 | 5.4 | 1.2 | 6.6 | 4.7 | nd | 1 | 2 |
| Lactobacillus farciminis + Lactobacillus plantarum | 36 | 42.5 | 6.0 | 0.9 | 6.9 | 4.5 | nd | 1 | 2 |
| Lactobacillus plantarum + sucrose | 37 | 42.5 | 5.3 | 1.1 | 6.4 | 4.7 | nd | 6 | 2 | nd: not determined

After 42.5 and 44 hours of incubation the following results were obtained, showing growth, sugar conversion and acid production:

| Strain | Exp No. | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|---|
| Lactobacillus plantarum | 1 | 35 | 7.3 | 1.0 | 8.3 | 4.4 | $1*10^{10}$ | 0 | 1.4 |
| Lactobacillus plantarum Inoc: $10^8$ CFU/g | 2 | 42.5 | 6.8 | 1.2 | 8.0 | 4.4 | $1*10^{10}$ | 0 | 1.8 |
| Lactobacillus plantarum (no α-gal) | 3 | 42.5 | 3.6 | 1.2 | 4.8 | 5.1 | $5*10^9$ | 0 | 0 |
| Lactobacillus plantarum Inoc: $10^7$ CFU/g | 4 | 42.5 | 7.3 | 1.5 | 8.8 | 4.6 | nd | 0 | 1.1 |
| Lactobacillus plantarum Inoc: $10^9$ CFU/g | 5 | 42.5 | 7.9 | 1.1 | 9.0 | 4.6 | nd | 0 | 1.25 |
| Lactobacillus plantarum | 6 | 52 | 6.6 | 1.2 | 7.8 | 4.5 | $1*10^{10}$ | 0 | 1.8 |
| Lactobacillus paracasei | 7 | 35 | 7.2 | 0.1 | 7.3 | 4.1 | $3*10^{10}$ | 0 | 2.4 |
| Lactobacillus paracasei | 8 | 42.5 | 6.6 | 0.1 | 6.7 | 4.2 | $2*10^{10}$ | 0.5 | 2.6 |
| Lactobacillus paracasei | 9 | 52 | 5.3 | 0.1 | 5.4 | 4.4 | $2*10^{10}$ | 3 | 3 |
| Bacillus coagulans | 10 | 35 | 6.9 | 1.2 | 8.1 | 4.5 | nd | 0 | 1.3 |
| Bacillus coagulans Inoc: $10^8$ CFU/g | 11 | 42.5 | 8.2 | 1.3 | 9.5 | 4.6 | $4*10^9$ | 0.4 | 1 |

-continued

| Strain | Exp No. | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|---|
| *Bacillus coagulans* (no α-gal) | 12 | 42.5 | 5.5 | 1.2 | 6.7 | 4.7 | 2*10$^9$ | 0 | 0 |
| *Bacillus coagulans* Inoc: 10$^7$ CFU/g | 13 | 42.5 | 7.3 | 1.3 | 8.6 | 4.7 | 3*10$^9$ | 0.5 | 1 |
| *Bacillus coagulans* | 14 | 55 | 3.7 | 0.8 | 4.5 | 5.1 | nd | 2 | 2 |
| *Bacillus licheniformis* | 15 | 35 | 2.7 | 0.0 | 2.7 | 5.1 | nd | 2.5 | 4 |
| *Bacillus licheniformis* | 16 | 42.5 | 0.8 | 0.0 | 0.8 | 6.0 | nd | 2.5 | 4 |
| *Bacillus licheniformis* | 17 | 55 | 0.2 | 0.0 | 0.2 | 6.4 | nd | 2.7 | 3.3 |
| *Bacillus subtilis* | 18 | 35 | 2.4 | 0.1 | 2.5 | 5.1 | nd | 3 | 4 |
| *Bacillus subtilis* | 19 | 42.5 | 2.5 | 0.9 | 3.4 | 5.3 | 3*10$^9$ | 3.6 | 2.6 |
| *Bacillus subtilis* | 20 | 55 | 0.5 | 0.1 | 0.6 | 6.0 | nd | 5 | 2 |
| *Lactobacillus fermentum* | 21 | 42.5 | 4.6 | 2.1 | 6.7 | 4.9 | 5*10$^{10}$ | 1 | 1 |
| *Lactobacillus acidophilus* | 22 | 42.5 | 4.2 | 0.2 | 4.4 | 4.7 | 4*10$^9$ | 1 | 1 |
| *Lactobacillus delbruckii bulgaricus* | 23 | 42.5 | 3.7 | 1.7 | 5.4 | 5.2 | 8*10$^9$ | 3.3 | 2.5 |
| *Lactobacillus farciminis* | 24 | 42.5 | 7.9 | 0.3 | 8.2 | 4.2 | 5*10$^9$ | 0.8 | 2.8 |
| *Lactobacillus formosensis* | 25 | 42.5 | 6.5 | 0.2 | 6.7 | 4.2 | 3*10$^9$ | 0.5 | 2 |
| *Lactococcus lactis* | 26 | 42.5 | 4.0 | 2.3 | 6.3 | 4.8 | 8*10$^9$ | 0.8 | 1 |
| *Bifidobacterium animalis* | 27 | 42.5 | 4.5 | 2.1 | 6.6 | 4.9 | 6*10$^9$ | 1 | 0.8 |
| *Pediococcus acidolactici* | 28 | 42.5 | 6.9 | 1.5 | 8.4 | 4.6 | 9*10$^9$ | 0.5 | 0.7 |
| *Enterococcus faecium* | 29 | 42.5 | 7.6 | 1.5 | 9.1 | 4.6 | 7*10$^9$ | 0.5 | 0.7 |
| *Enterococcus faecalis* | 30 | 42.5 | 5.8 | 1.5 | 7.3 | 4.7 | 9*10$^9$ | 0.3 | 0.3 |
| *Enterococcus durans* | 31 | 42.5 | 2.7 | 0/2 | 2.9 | 4.9 | 2*10$^9$ | 3 | 2 |
| *Weisella hellenica* | 32 | 42.5 | 4.1 | 1.6 | 5.7 | 4.9 | 3*10$^9$ | 1 | 1 |
| *Lactobacillus salivarius* + *Lactobacillus paracasei* | 33 | 42.5 | 6.2 | 0.1 | 6.3 | 4.2 | 1*10$^{10}$ | 1 | 1.9 |
| *Streptococcus thermosphiles* + *Bifidobacterium animalis* | 34 | 42.5 | 5.1 | 2.0 | 7.1 | 4.8 | 8*10$^{10}$ | 0.2 | 1 |
| *Pediococcus acidolactici* + *Lactobacillus plantarum* | 35 | 42.5 | 6.9 | 1.2 | 8.1 | 4.4 | 1*10$^{10}$ | 0 | 1 |
| *Lactobacillus farciminis* + *Lactobacillus plantarum* | 36 | 42.5 | 7.4 | 1.0 | 8.4 | 4.4 | 9*10$^9$ | 0 | 1.4 |
| *Lactobacillus plantarum* + sucrose | 37 | 42.5 | 6.5 | 1.0 | 7.5 | 4.4 | 1*10$^{10}$ | 4 | 2.2 | nd: not determined

After 116 hours of incubation the following results were obtained, showing sugar conversion and acid production.

| Strain | Exp. No. | DM % | Lactic acid % of DM | Acetic acid % of DM | Total acid % of DM | pH | Sucrose % of DM | Galactose % of DM |
|---|---|---|---|---|---|---|---|---|
| Bacillus coagulans | 10 | 35 | 7.7 | 1.2 | 8.9 | 4.3 | 0 | 0 |
| Bacillus coagulans | 11 | 42.5 | 7.7 | 1.2 | 8.9 | 4.3 | 0.1 | 0.5 |
| Bacillus coagulans | 14 | 55 | 4.8 | 0.7 | 5.5 | 4.8 | 1.2 | 1.6 |
| Bacillus licheniformis | 15 | 35 | 2.5 | 0.1 | 2.6 | 4.8 | 0.3 | 3.5 |
| Bacillus licheniformis | 16 | 42.5 | 1.7 | 0.1 | 1.8 | 5.5 | 2 | 3.3 |
| Bacillus licheniformis | 17 | 55 | 0.4 | 0.1 | 0.5 | 6.3 | 2.9 | 3.3 |
| Bacillus subtilis | 18 | 35 | 1.6 | 0.1 | 1.7 | 4.9 | 0 | 3.5 |
| Bacillus subtilis | 19 | 42.5 | 1.4 | 0.1 | 1.5 | 5.1 | 1.5 | 3.5 |
| Bacillus subtilis | 20 | 55 | 0.8 | 0.2 | 1.0 | 5.9 | 5 | 3 |

Example 6

Testing Different Production Organisms at 44° C., at 40% DM

Experimental Set-Up:

| Strain | Dry matter % of weight | Inoculation level CFU/g DM | SBM 88% DM g | α-galactosidase mg | Water Ml |
|---|---|---|---|---|---|
| Lactobacillus plantarum | 40 | $1*10^8$ | 68.2 | 72 | 73 |
| Pediococcus acidolactici | 40 | $1*10^8$ | 68.2 | 72 | 73 |
| Bacillus coagulans | 40 | $1*10^8$ | 68.2 | 72 | 73 |
| Bacillus licheniformis | 40 | $1*10^8$ | 68.2 | 72 | 73 |
| Bacillus subtilis | 40 | $1*10^8$ | 68.2 | 72 | 73 |

Samples were incubated in a 44° C. thermostatic water bath.

Results:

After 20 hours of incubation the following results were obtained, showing growth, sugar conversion and acid production:

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| Lactobacillus plantarum | 40 | 5.1 | 0.2 | 5.3 | 4.8 | Nd | 3 | 2.5 |
| Pediococcus acidolactici | 40 | 4.7 | 0.2 | 4.9 | 4.8 | Nd | 3 | 3 |
| Bacillus coagulans | 40 | 4.4 | 0.1 | 4.5 | 5.0 | $2*10^{10}$ | 2 | 2.5 |
| Bacillus licheniformis | 40 | 1.1 | 0.0 | 1.1 | 6.0 | $2*10^8$ | 2.5 | 3.6 |
| Bacillus subtilis | 40 | 0.7 | 0.2 | 0.9 | 6.0 | $1*10^9$ | 6.5 | 3.8 | nd: not determined

After 44 hours of incubation the following results were obtained, showing sugar conversion and acid production (CFU not determined):

| Strain | DM % | Lactic acid % of DM | Acetic acid % of DM | Total acid % of DM | pH | Sucrose % of DM | Galactose % of DM |
|---|---|---|---|---|---|---|---|
| *Lactobacillus plantarum* | 40 | 6.8 | 0.3 | 7.1 | 4.4 | 3 | 2.2 |
| *Pediococcus acidolactici* | 40 | 6.6 | 0.3 | 6.9 | 4.4 | 2 | 1.5 |
| *Bacillus coagulans* | 40 | 7.2 | 0.2 | 7.4 | 4.4 | 0.5 | 1.0 |
| *Bacillus licheniformis* | 40 | 1.5 | 0.1 | 1.6 | 5.9 | 1 | 2.9 |
| *Bacillus subtilis* | 40 | 1.3 | 0.1 | 1.4 | 5.7 | 4.5 | 2.9 |

Example 7

Testing Different Production Organisms at 52° C., at 52% DM

Experimental Set-Up:

| Strain | Dry matter % of weight | Inoculation level CFU/g DM | SBM (88% DM) g | α-galactosidase mg | Water Ml |
|---|---|---|---|---|---|
| *Bacillus smithii* | 42.5 | $1*10^8$ | 113.6 | 120 | 172 |
| *Bacillus smithii* | 42.5 | $1*10^8$ | 113.6 | No addition | 172 |
| *Bacillus licheniformis* | 42.5 | $1*10^8$ | 113.6 | 120 | 172 |
| *Bacillus licheniformis* | 42.5 | $1*10^8$ | 113.6 | No addition | 172 |
| *Bacillus coagulans* | 42.5 | $1*10^8$ | 113.6 | 120 | 172 |

Samples were incubated in a 52° C. thermostatic water bath.

Results:

After 116.5 hours of incubation the following results were obtained, showing growth, sugar conversion and acid production

| Strain | DM % | Lactic acid % of DM | Acetic acid % of DM | Total acid % of DM | pH | Inoculation level CFU/g DM | Sucrose % of DM | Galactose % of DM |
|---|---|---|---|---|---|---|---|---|
| *Bacillus smithii* | 42.5 | 3.3 | 0.1 | 3.4 | 5.2 | $1*10^6$ | 4 | 2 |
| *Bacillus smithii* (no α-gal) | 42.5 | 2.2 | 0.1 | 2.3 | 5.3 | Nd | 2 | 0 |
| *Bacillus licheniformis* | 42.5 | 3.8 | 0 | 3.8 | 5.4 | $5*10^7$ | 3 | 2 |
| *Bacillus licheniformis* (no α-gal) | 42.5 | 2.7 | 0 | 2.7 | 5.5 | Nd | 0.5 | 0 |
| *Bacillus coagulans* | 42.5 | 1.8 | 0.2 | 2.0 | 4.9 | $4*10^8$ | 1.5 | 1.5 | nd: not determined

Example 8

Testing Different Production Organisms at 60° C.
Experimental Set-Up:

| Strain | Dry matter % of weight | Inoculation level CFU/g DM | SBM (88% DM) g | α-galactosidase mg | Water Ml |
|---|---|---|---|---|---|
| Bacillus coagulans | 42.5 | $1*10^8$ | 113.6 | 120 | 122 |
| Bacillus smithii | 42.5 | $1*10^8$ | 113.6 | 120 | 122 |
| Geobacillus thermodenitrificans | 35 | $1*10^8$ | 113.6 | 120 | 172 |

Samples were incubated in a 60° C. incubator.
Results:
After 44.5 and 116.5 hours of incubation the following results were obtained, showing growth, sugar conversion and acid production

| Strain | Incubation Time Hours | DM % | Lactic acid % of DM | Acetic acid % of DM | Total acids % of DM | pH | Inoculation level CFU/g DM | Sucrose % of DM | Galactose % of DM |
|---|---|---|---|---|---|---|---|---|---|
| Bacillus coagulans | 116.5 | 42.5 | 1.3 | 0.2 | 1.5 | 5.3 | $6*10^6$ | 7 | 4 |
| Bacillus smithii | 116.5 | 42.5 | 0.8 | 0.4 | 1.2 | 5.7 | $5*10^6$ | 7 | 4 |
| Geobacillus thermodenitrificans | 44.5 | 35 | 2.0 | 0.2 | 2.2 | 5.2 | $9*10^7$ | 8 | 4 |

Example 9

Bioconversion with Alternative Biomasses
Incubation at 37° C. for 42.5 to 45.5 hours

| Strain | Dry matter % of weight | Inoculation level CFU/g DM | SBM (88% DM) g | RSM (88% DM) g | SSM (91% DM) g | α-galactosedase mg | Water Ml |
|---|---|---|---|---|---|---|---|
| Lactobacillus plantarum | 35 | $1*10^8$ | 113.6 | — | — | 120 | 172 |
| Lactobacillus plantarum | 42.5 | $1*10^8$ | 113.6 | — | — | 120 | 122 |
| Lactobacillus plantarum | 52 | $1*10^8$ | 113.6 | — | — | 120 | 79 |
| Lactobacillus plantarum | 35 | $1*10^8$ | 90.1 | 22.8 | — | 120 | 172 |
| Lactobacillus plantarum | 42.5 | $1*10^8$ | 90.1 | 22.8 | — | 120 | 122 |
| Lactobacillus plantarum | 52 | $1*10^8$ | 90.1 | 22.8 | — | 120 | 79 |
| Lactobacillus plantarum | 35 | $1*10^8$ | 67.8 | — | 43.8 | 120 | 174 |
| Lactobacillus plantarum | 42.5 | $1*10^8$ | 67.8 | — | 43.8 | 120 | 124 |
| Lactobacillus plantarum | 52 | $1*10^8$ | 67.8 | — | 43.8 | 120 | 81 |
| Bacillus coagulans | 35 | $1*10^8$ | 68.2 | — | — | 72 | 103 |
| Bacillus coagulans | 42.5 | $1*10^8$ | 113.6 | — | — | 120 | 122 |
| Bacillus coagulans | 55 | $1*10^8$ | 68.2 | — | — | 72 | 41 |

| Strain | Dry matter % of weight | Inoculation level CFU/g DM | SBM (88% DM) g | RSM (88% DM) g | SSM (91% DM) g | α-galactosedase mg | Water Ml |
|---|---|---|---|---|---|---|---|
| Bacillus coagulans | 35 | 1*10$^8$ | 90.1 | 22.8 | — | 120 | 172 |
| Bacillus coagulans | 42.5 | 1*10$^8$ | 90.1 | 22.8 | — | 120 | 122 |
| Bacillus coagulans | 52 | 1*10$^8$ | 90.1 | 22.8 | — | 120 | 79 |
| Bacillus coagulans | 35 | 1*10$^8$ | 67.8 | — | 43.8 | 120 | 174 |
| Bacillus coagulans | 42.5 | 1*10$^8$ | 67.8 | — | 43.8 | 120 | 124 |
| Bacillus coagulans | 52 | 1*10$^8$ | 67.8 | — | 43.8 | 120 | 81 |

Results:

After 42.5 to 45.5 hours of incubation the following results were obtained, showing growth, sugar conversion and acid production

| Strain | DM % | Bio-mass | Lactic acid % of DM | Acetic acid % of DM | Total acids % of DM | pH | Inoculation level CFU/g DM | Sucrose % of DM | Galactose % of DM |
|---|---|---|---|---|---|---|---|---|---|
| Lactobacillus plantarum | 35 | SBM | 7.2 | 0.1 | 7.3 | 4.1 | 3*10$^{10}$ | 0 | 2.4 |
| Lactobacillus plantarum | 42.5 | SBM | 6.8 | 1.2 | 8.0 | 4.4 | 1*10$^{10}$ | 0 | 1.8 |
| Lactobacillus plantarum | 52 | SBM | 6.6 | 1.2 | 7.8 | 4.5 | 1*10$^{10}$ | 0 | 1.8 |
| Lactobacillus plantarum | 35 | SBM/RSM | 7.3 | 0.9 | 8.2 | 4.4 | 5*10$^9$ | 0 | 1 |
| Lactobacillus plantarum | 42.5 | SBM/RSM | 6.8 | 1.0 | 7.8 | 4.4 | 5*10$^9$ | 0 | 1 |
| Lactobacillus plantarum | 52 | SBM/RSM | 5.9 | 0.9 | 6.8 | 4.5 | 7*10$^9$ | 0.8 | 1 |
| Lactobacillus plantarum | 35 | SBM/SSM | 6.5 | 0.7 | 7.2 | 4.4 | 4*10$^9$ | 0 | 1 |
| Lactobacillus plantarum | 42.5 | SBM/SSM | 6.3 | 0.7 | 7.0 | 4.4 | 4*10$^9$ | 0 | 1 |
| Lactobacillus plantarum | 52 | SBM/SSM | 5.7 | 0.7 | 6.4 | 4.4 | 4*10$^9$ | 0.8 | 1 |
| Bacillus coagulans | 35 | SBM | 6.9 | 1.2 | 8.1 | 4.5 | nd | 0 | 1.3 |
| Bacillus coagulans | 42.5 | SBM | 6.5 | 1.3 | 7.8 | 4.5 | 7*10$^9$ | 0 | 0.5 |
| Bacillus coagulans | 55 | SBM | 3.7 | 0.8 | 4.5 | 5.1 | nd | 2 | 2 |
| Bacillus coagulans | 35 | SBM/RSM | 7.2 | 0.9 | 8.1 | 4.4 | 2*10$^9$ | 0 | 0.5 |
| Bacillus coagulans | 42.5 | SBM/RSM | 6.3 | 1.0 | 7.3 | 4.4 | 3*10$^9$ | 0.3 | 0.8 |
| Bacillus coagulans | 52 | SBM/RSM | 5.6 | 0.9 | 6.5 | 4.5 | 2*10$^9$ | 1 | 1 |
| Bacillus coagulans | 35 | SBM/SSM | 6.1 | 0.7 | 6.8 | 4.4 | 2*10$^9$ | 0 | 0 |
| Bacillus coagulans | 42.5 | SBM/SSM | 5.8 | 0.7 | 6.5 | 4.4 | 5*10$^9$ | 0.3 | 0.5 |
| Bacillus coagulans | 52 | SBM/SSM | 4.7 | 0.7 | 5.4 | 4.6 | 3*10$^9$ | 1 | 1 |

Example 10

Pilot Scale Bioconversion

Incubator:

The incubator was a pilot scale vertical reactor with a total volume of 2.0 m$^2$. The incubator was equipped with a temperature probe at the inlet as well as at the outlet.

Incubation Mixture:

The incubator was incubated with a preheated mixture of 250 kg soya bean meal (88% DM); 264 g α-galactosidase from Bio-Cat (12,500 U/g), dry formulation of Bacillus coagulans to reach a final inoculation level of 1*10$^7$ cells/g DM, and 268 litre tap water. The ratio wet bulk density/dry bulk density of the incubation mixture was 0.88. This resulted in a DM of 42.5% of the incubation mixture.

Test Procedure:

After filling of the reactor, it was flushed with N$_2$ gas, to get rid of O$_2$. The biomass was incubated at 60 hours at 37° C.

Results:

After 60 hours a product comprising 7.5% of DM lactic acid and 1.3% of DM acetic acid was obtained.

pH had dropped to 4.6.

Example 11

Large Scale Bioconversion

Incubator:

The reactor used was a vertical cylinder with an effective height of 7.3 m and a diameter of 4.3 m.

In the top of the vertical reactor, the feed mixture falls on position near the centre of the reactor. For even distribution, a scraper blade or level arm distributes the inlet feed mixture over the perimeter of reactor.

In the bottom of the reactor, the product was extracted by means to achieve a uniform residence time for any particle spread on the top of the reactor.

Testing Uniform Plug Flow

The inlet and outlet means of the reactor were adjusted to achieve an expected residence time of 12 hours. For proving the uniform distribution time, an inert tracer substance was added to the feed mixture. The feed mixture used in the experiment had a natural content of iron of around 143 mg/kg dry matter (=off-set concentration); therefore, iron sulphate ($FeSO_4$) was used as a tracer in a concentration of 1167 mg $FeSO_4$/kg feed mixture dry matter equal to a total iron content of 572 mg Fe/kg total dry matter. At time 0 hours, $FeSO_4$ was added to the feed mixture dosed to the reactor for a period of 60 minutes. Samples were drawn every 20 minutes, dried, and analysed for content of iron, and it was found that the $FeSO_4$ enriched product leaves the reactor 12-13 hours after dosing $FeSO_4$ to the inlet feed mixture, and a maximum concentration of 355 mg/kg Fe was found at 12.5 hours after start.

The invention claimed is:

1. A method for producing a solid transformation product of a biomass substrate, wherein the solid transformation product is a product of the transformation of one or more of proteinaceous matter and carbohydrates originating from a biomass substrate, the method comprising:
    (a) preparing a substrate of a biomass comprising carbohydrates and proteinaceous matter that originate from soya bean seed, rape seed, or mixtures thereof, wherein at least 20% by weight of said biomass comprises carbohydrates and proteinaceous matter originating from soya bean seeds, rape seeds, or mixtures thereof, optionally in further mixture with carbohydrates and proteinaceous matter originating from one or more of seeds of fava beans, seeds of peas, sunflower seeds, seeds of lupine, cereals, and grasses;
    (b) mixing said substrate with a live microorganism or a combination of live microorganisms, which live microorganism or combination of live microorganisms is not, and does not comprise, live yeast, and adding water in an amount which provides an initial incubation mixture having a water content from 30% to 70% by weight, and a ratio of wet bulk density to dry bulk density from 0.60 to 1.45;
    (c) incubating said initial incubation mixture for 1-240 hours at a temperature of 15-70° C., and
    (d) recovering solid transformation product from the incubated mixture;
    wherein the incubating step is performed as a continuous plug-flow process in a vertical, non-agitated incubation tank with an inlet for said feed mixture and additives and an outlet for said solid transformation product, and wherein transport of the biomass is mediated by gravitational force.

2. The method according to claim 1, further comprising pre-treating said substrate before mixing with said live microorganism or said combination of live microorganisms by one or more selected from disintegration, milling, flaking, heat treatment, pressure treatment, ultrasonic treatment, hydrothermal treatment, acid treatment and alkaline treatment.

3. The method according to claim 1, wherein at least 30% by weight of said biomass comprises carbohydrates and proteinaceous matter originating from one or more of optionally defatted and optionally dehulled soya bean seeds, optionally defatted rape seeds, and mixtures thereof.

4. The method according to claim 3, wherein the weight of said biomass comprising carbohydrates and proteinaceous matter originating from optionally defatted and/or optionally dehulled soya bean seeds, optionally defatted rape seeds, or mixtures thereof is selected from at least 40%, at least 50%, at least 60%, at least 70%, at least 80%, and at least 90% by weight of said biomass.

5. The method according to claim 1, wherein said biomass comprises one or more of oligosaccharides and polysaccharides, and optionally further comprises oils and fats.

6. The method according to claim 1, wherein said solid transformation product is a product of the transformation of proteinaceous matter, or of the transformation of carbohydrates, or of the transformation of proteinaceous matter and carbohydrates originating from seeds of soya, pea, lupine, or sunflower, or from wheat, maize, or rape seed.

7. The method according to claim 1, wherein the live microorganism or combination of live microorganisms is one or more microorganisms which can produce one or more organic acids from carbohydrates selected from formic acid, acetic acid, propionic acid, butyric acid, lactic acid, and succinic acid.

8. The method according to claim 1, wherein the live microorganism or combination of live microorganisms is one or more microorganisms which can produce one or more alcohols from carbohydrates.

9. The method according to claim 1, wherein the live microorganism or combination of live microorganisms is of a genus selected from:
    *Lactobacillus*
    *Lactococcus*
    *Streptococcus*
    *Pediococcus*
    *Enterococcus*
    *Leuconostoc*
    *Weisella*
    *Bifidobacterium*
    *Bacillus*
    *Brevibacillus*
    *Propionibacterium*
    *Clostridium*
    *Trichoderma*
    and
    *Aspergillus*.

10. The method according to claim 1, wherein the live microorganism or combination of live microorganisms is selected from one or more of *Lactobacillus, Pediococcus, Enterococcus, Lactococcus, Streptococcus*, and *Weisella* strains, and wherein the initial incubation mixture is incubated at a temperature of 15-50° C.

11. The method according to claim 1, wherein the live microorganism or combination of live microorganisms is selected from *Bacillus* strains, and wherein the initial incubation mixture is incubated a temperature of 20-60° C.

12. The method according to claim 1, wherein the live microorganism or combination of live microorganisms is selected from *Bifidobacterium* strains, and wherein the initial incubation mixture is incubated at a temperature of 20-45° C.

13. The method according to claim 1, wherein said initial incubation mixture is incubated for 2 to 180 hours.

14. The method according to claim 1, wherein water is added to said substrate in an amount which provides an initial incubation mixture having a ratio of wet bulk density to dry bulk density from 0.65 to 1.40.

15. The method according to claim 1, wherein water is added to said substrate of biomass in an amount which provides an initial incubation mixture having a ratio of wet bulk density to dry bulk density selected from 0.70, 0.75, 0.80, 0.85, 0.90, 0.95, 1.00, 1.10, 1.15, 1.20, 1.25, 1.30, and 1.35.

16. The method according to claim 1, wherein the water content in said initial incubation mixture is from 35% to 70% by weight.

17. The method according to claim 1, wherein the water content in said initial incubation mixture is selected from 40%, 45%, 50%, 55%, 60%, and 65%.

18. The method according to claim 1, wherein said live microorganism or combination of live microorganisms is used in an amount of $10^3$ to $10^{11}$ CFU (colony forming units) per g of said substrate.

19. The method according to claim 1, further comprising adding one or more processing aids selected from enzymes, plant components, and organic and inorganic processing agents to one or more of the substrate and the initial incubation mixture.

20. The method according to claim 1, further comprising adding α-galactosidase to one or more of the substrate and the initial incubation mixture.

21. The method according to claim 1, further comprising adding an α-galactosidase preparation to one or more of the substrate and the initial incubation mixture in an amount of from 0.05 to 50 α-galactosidase units per g dry matter of the substrate.

22. The method according to claim 1, wherein the vertical, non-agitated incubation tank is closed.

23. The method according to claim 1, wherein said incubation is carried out under anaerobic conditions.

24. The method according to claim 1, wherein said non-agitated incubation tank is of a vertical, oblong cylindrical or polyhedral type.

25. The method according to claim 1, wherein the area in the upper part of said non-agitated incubation tank is less than the area in the lower part.

26. The method according to claim 1, where said non-agitated incubation tank has insulating matting or a thermal dimple jacket.

27. The method according to claim 1, wherein the filling degree of said incubation tank is kept constant.

* * * * *